(12) United States Patent
Khaleghi et al.

(10) Patent No.: US 12,740,706 B2
(45) Date of Patent: Sep. 22, 2026

(54) MEDICAL IMPLANT WITH WIRELESS COMMUNICATION

(71) Applicant: OSLO UNIVERSITETSSYKEHUS HF, Nydalen (NO)

(72) Inventors: Ali Khaleghi, Trondheim (NO); Ilangko Balasingham, Oslo (NO)

(73) Assignee: OSLO UNIVERSITETSSYKEHUS HF, Oslo (NO)

( * ) Notice: Subject to any disclaimer, the term of this patent is extended or adjusted under 35 U.S.C. 154(b) by 1380 days.

(21) Appl. No.: 16/961,726

(22) PCT Filed: Jan. 17, 2019

(86) PCT No.: PCT/EP2019/051166
§ 371 (c)(1),
(2) Date: Jul. 13, 2020

(87) PCT Pub. No.: WO2019/141782
PCT Pub. Date: Jul. 25, 2019

(65) Prior Publication Data

US 2021/0059526 A1 Mar. 4, 2021

(30) Foreign Application Priority Data

Jan. 18, 2018 (GB) ..................................... 1800820

(51) Int. Cl.
*A61B 5/00* (2006.01)
*A61B 5/145* (2006.01)
*H01Q 1/27* (2006.01)

(52) U.S. Cl.
CPC .......... *A61B 5/0015* (2013.01); *A61B 5/0028* (2013.01); *A61B 5/0031* (2013.01); *A61B 5/14532* (2013.01); *H01Q 1/273* (2013.01)

(58) Field of Classification Search
CPC ... A61B 5/0015; A61B 5/0028; A61B 5/0031; A61B 5/14532; A61B 5/14539;
(Continued)

(56) References Cited

U.S. PATENT DOCUMENTS 8,155,586 B2 4/2012 Kim
9,672,393 B1 * 6/2017 Zhu ..................... A61N 1/3787
(Continued)

FOREIGN PATENT DOCUMENTS

GB 18008201 3/2018
JP 2002345765 * 12/2002
(Continued)

OTHER PUBLICATIONS

Machine Translation of JP 2002345765, Patent Translate, pp. 1-21, printed on Sep. 6, 2023, (Year: 2002).*
(Continued)

*Primary Examiner* — Jennifer Robertson
*Assistant Examiner* — Om Patel
(74) *Attorney, Agent, or Firm* — CANTOR COLBURN LLP

(57) ABSTRACT

An implant device 12 for use within the body comprises: a data source; and a non-self-resonant antenna for backscatter communications with an external communication system. The non-self-resonant antenna comprises at least two electrodes 16 including two conductive patches 16 that are arranged to be spaced apart when the implant device 12 is in use The implant device 12 is arranged to control the backscattering properties of the non-self-resonant antenna in order to thereby transmit data from the data source to the external communications system. The implant device 12 is arranged such that the backscattering properties of the non-self-resonant antenna are controlled by one or more electrical switch(es) 14 including an electrical switch that is
(Continued)

arranged to change the impedance of the non-self-resonant antenna by switching between coupling the at least two electrodes 16 via body tissue 18 and coupling the at least two electrodes 16 via a conductive pathway.

20 Claims, 6 Drawing Sheets

(58) Field of Classification Search
CPC ..... A61B 5/1459; A61B 5/073; A61B 5/1473; A61B 5/4238; A61B 5/4833; A61B 2560/0219; A61B 1/00016; A61B 1/00029; A61B 5/686–6861; A61B 2562/162; H01Q 1/273; H01Q 15/148; A61F 2250/0002
See application file for complete search history.

(56) References Cited

U.S. PATENT DOCUMENTS

2004/0257220 A1 12/2004 Fischer
2005/0154428 A1 7/2005 Bruinsma
2006/0097918 A1 5/2006 Oshiyama
2006/0173265 A1 8/2006 Kim
2007/0123772 A1 5/2007 Euliano
2007/0221233 A1 9/2007 Kawano
2007/0288066 A1 12/2007 Christman et al.
2009/0005656 A1 1/2009 Najafi
2009/0043183 A1* 2/2009 Kermani .................. A61F 2/82 623/1.15
2009/0137883 A1 5/2009 Chiba
2009/0248112 A1 10/2009 Mumbru et al.
2010/0198142 A1* 8/2010 Sloan .................... G16H 20/10 345/173
2012/0008714 A1 1/2012 Rizwan
2012/0203079 A1* 8/2012 McLaughlin .......... A61B 5/316 600/377
2013/0085537 A1 4/2013 Mashiach
2013/0215979 A1 8/2013 Yakovlev
2013/0338452 A1 12/2013 Robertson
2014/0031837 A1 1/2014 Perryman et al.
2014/0055088 A1 2/2014 Joshi
2014/0084855 A1 3/2014 Joshi
2014/0180365 A1 6/2014 Perryman et al.
2014/0207149 A1 7/2014 Hastings
2014/0222110 A1 8/2014 Kibler
2014/0225804 A1 8/2014 Wild
2014/0358196 A1* 12/2014 Mashiach ............ A61N 1/3606 607/60
2014/0361080 A1 12/2014 Baym
2015/0112160 A1 4/2015 Gazdzinski
2015/0119659 A1 4/2015 Gazdzinski
2015/0182463 A1 7/2015 Hafezi
2015/0311944 A1 10/2015 Gollakota
2015/0364822 A1 12/2015 O'Driscoll
2016/0092706 A1 3/2016 Deyle
2016/0094933 A1 3/2016 Deyle
2016/0135688 A1 5/2016 Kappel
2016/0190698 A1 6/2016 Andresen
2017/0095667 A1* 4/2017 Yakovlev ............. A61B 5/0022
2017/0126282 A1 5/2017 Fromm
2017/0187250 A1 6/2017 Cha
2017/0224248 A1* 8/2017 Zou ........................ A61B 5/061
2017/0270779 A1 9/2017 Zdeblick
2018/0034137 A1 2/2018 Lebaron
2020/0091608 A1 3/2020 Alpman et al.

FOREIGN PATENT DOCUMENTS

JP 2004538058 * 1/2004
WO WO-0137726 A1 * 5/2001 ........... A61B 5/0031
WO WO-2009111009 A1 * 9/2009 ......... A61N 1/37229
WO 2010051389 A1 5/2010
WO WO-2010077897 A1 * 7/2010 ......... A61N 1/37229
WO 2011111008 A1 9/2011
WO 2013046032 A2 4/2013
WO WO-2016051206 A1 * 4/2016 ............... A61N 1/05
WO 2017044904 A1 3/2017
WO WO-2017136767 A1 * 8/2017 ............. H01Q 1/273
WO 2017154178 A1 9/2017
WO 2018011235 A1 1/2018
WO WO-2018009905 A2 * 1/2018 ........... A61B 5/0031
WO 2019141782 A1 7/2019

OTHER PUBLICATIONS

Machine Translation of JP 2004538058, Patent Translate, pp. 1-24, printed on Mar. 26, 2024 (Year: 2004).*
A. Khaleghi et al. "Wireless Communication Link for Capsule Endoscope at 600 MHZ", 37th Annual International Conference of the IEEE Engineering in Medicine and Biology Society (EMBC) 2015, pp. 4081-4084.
British Search Report for corresponding application GB1612175.8; Report Dated Dec. 16, 2016.
Hamidrez Memarzadeh-Tehran, et al. "A Dual-Band Meander Monopole Antenna for On-Body Devices", Antennas and Propagation (APSURSI), IEEE International Symposium, 2011, pp. 160-163.
International Search Report for corresponding application PCT/EP2017/067461 filed Jul. 11, 2017; Mail date Nov. 13, 2017.
International Search Report for corresponding application PCT/EP2019/051166 filed Jan. 17, 2019; Mail date Apr. 17, 2019.
Search Report from IPO for corresponding application GB1800820.1; Report dated Jun. 22, 2018.
Stewart J. Thomas et al. "Modulated Backscatter for Ultra-Low Power Uplinks from Wearable and Implantable Devices", Proceedings of the 2012 ACM workshop on Medical communication systems, pp. 1-6.
Written Opinion for corresponding application PCT/EP2019/051166 filed Jan. 17, 2019; Mail date Apr. 17, 2019.
Written Opinion of the International Searching Authority for corresponding application PCT/EP2017/067461 filed Jul. 11, 2017; Mail date Nov. 13, 2017.
Yoshiya Saito et al. "Low-Profile and Electrically Small Meander-Line Antenna Using a Capacitive Feed Structure", IEEE Antennas and Wireless Propagation Letters, 2012, vol. 11, pp. 1281-1284.
Ali Ibraheem, "Intra-Body Propagation Channel Investigation Using Electrically Coupled Loop Antenna", Progress in Electromagnetic Research M, vol. 40, 57-67, 2014.
British Search Report for corresponding application 1913086.3; Report Jul. 24, 2020.
Written Opinion for corresponding application PCT/EP2020/075383 filed Sep. 10, 2020; Mail date Oct. 28, 2020.
International Search Report for corresponding application PCT/EP2020/075383 filed Sep. 10, 2020; Mail date Oct. 28, 2020.
Communication Received from European Patent Office for corresponding application 19700934.3; Report dated Dec. 20, 2022.
Gary Breed, "The Fundamentals of Patch Antenna Design and Performance," High Frequency Electronics, Mar. 2009, p. 48-51.
Mailadil T. Sebastian, "Measurement of Microwave Dielectric Properties and Factors Affecting Them" Dielectric Materials for Wireless Communication, p. 11, 2008.

* cited by examiner

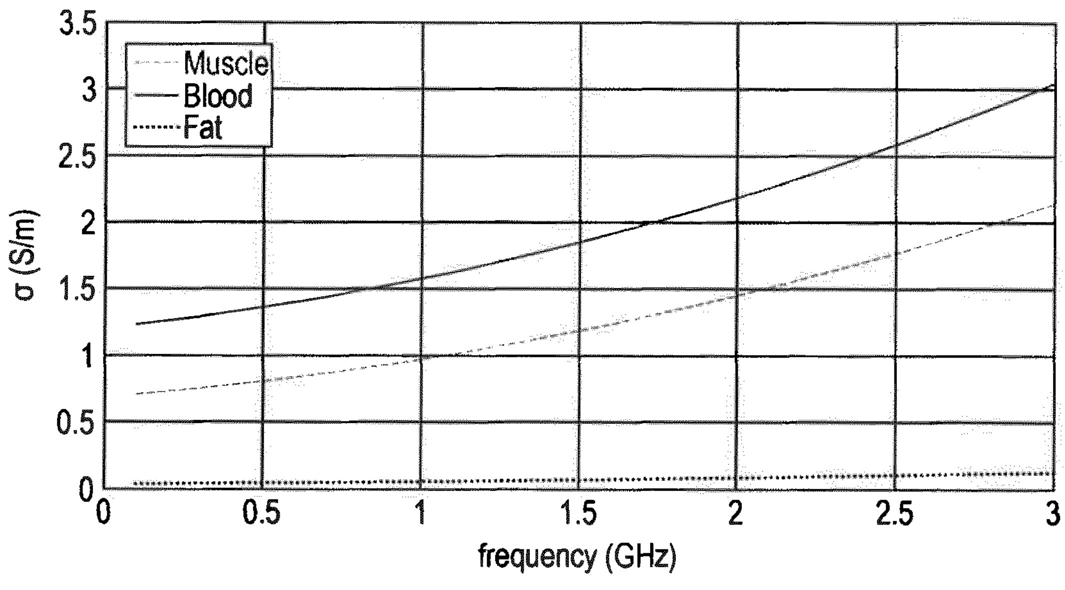
Fig. 1
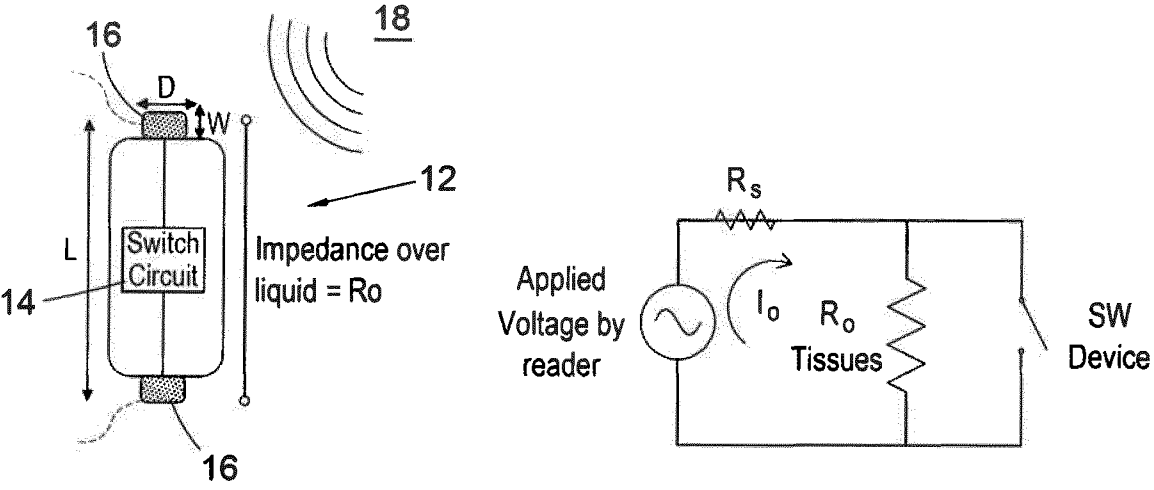
Fig. 2
Fig. 3

MEDICAL IMPLANT WITH WIRELESS COMMUNICATION

The present invention relates to a medical implant arranged for wireless communication from within the body, and to a system for communication with the implant, as well as to related methods.

Medical implants are used to gather information about the body and to interact with the body in various contexts. For example, capsule endoscopes are used to gather images within the digestive systems as well as to obtain samples or deliver drugs, neural prosthetic systems link the brain with external devices and exchange electrical signals with the brain, cardiac pacemakers or cardiac leadless pacemakers are used to synchronize the heart beats and various other devices have been proposed that rely on being held within the body or passed through the body. For all of these medical implant devices it provides advantages if there can be wireless communication with other devices outside or inside the body. This may be for wireless control or programming of the implant, for transmission of data from sensors such as cameras, temperature sensors, blood monitoring sensors and the like, and other things.

Typical data transfer rates and the depth of the implant beneath the body surface are set out in the table below. Wireless data transmission within these ranges is highly desirable in order to allow for fully wireless operation of the implant. In fact for some applications it is impossible to have a wired connection from out of the body to the implant, and difficult as well as inconvenient to have a wired link to a separate implanted transmitter device closer to the body surface (as is used in some cases for neural prosthetics).

| Application | Required data rate | Range |
|---|---|---|
| Capsule endoscope (video streaming) | 1-100 Mbps | 30-150 mm |
| Heart monitoring | 40-200 Kbps | 100 mm |
| Neural monitoring | 512 sensors, 430 Mbps | 20-30 mm |

For a fully wireless connection from outside the body to the location of the implant device challenges can be generated both by the need for a minimum data transfer rate and by the depth of the body tissue.

Implant devices with wireless communication capabilities and also wireless power transfer have been proposed in the prior art. For example, US 2013/0215979 describes a method for simultaneous power and data transfer from the exterior of the body to an implant device. A circuit at the implant device is used for power harvesting from the exterior RF signal and there may be backscatter communication from the implant to the exterior device. Load modulation is proposed for transmitting a data signal back to the exterior device. A part of the charging RF signal is used for backscatter communication and the remainder is used for the wireless power transfer.

US 2014/0055088 describes a method for wireless charging of an implant device. The backscatter from the communication coil is used to indicate the best frequency for efficient charging. Thus the external transmitter can adjust its frequency for wireless power transfer based on a rudimentary feedback mechanism using backscattered information.

US 2014/0084855 discusses wireless power transfer and data transmission to an implant (from exterior to implant). A backscatter signal is received in the exterior system and is processed in order to either control the implant impedance matching unit or to alter the frequency of the exterior device. In both cases this is done in order to obtain maximum wireless power transfer.

None of these existing devices can fully satisfy the ideal requirements for data transfer rates and also penetrate sufficiently deep into the body. There is a need for a more effective way to communicate with medical implants, and in particular to increase the possible depth of body tissue for which communications can be effective, whilst at the same time avoiding undue use of the implant device's internal power supply. The ability to communicate reliably with implant devices at locations deeper within the body would greatly enhance the utility of wireless data transmission for medical implants.

Viewed from a first aspect, the invention provides an implant device for use within the body, the implant device comprising: a data source; and a non-self-resonant antenna for backscatter communications with an external communication system, the non-self-resonant antenna comprising at least two electrodes including two conductive patches that are arranged to be spaced apart when the implant device is in use; wherein the implant device is arranged to control the backscattering properties of the non-self-resonant antenna in order to thereby transmit data from the data source to the external communications system; and wherein the implant device is arranged such that the backscattering properties of the non-self-resonant antenna are controlled by one or more electrical switch(es) including an electrical switch that is arranged to change the impedance of the non-self-resonant antenna by switching between coupling the at least two electrodes via body tissue and coupling the at least two electrodes via a conductive pathway.

With this combination of features the non-self-resonant antenna can be controlled with very low power required from the implant device and with the possibility of a high change in antenna impedance, which allows for effective backscattering communication with an external transmitter/receiver system, which would generally include antennas outside of the body. The use of a non-self-resonant antenna allows for a large radar cross section (RCS) and hence for efficient backscatter performance. The switch changes the impedance of the non-self-resonant antenna by changing the degree to which the surrounding body tissue impacts on the effective impedance of the antenna. Thus, the switch can be open in order that the body tissue is a primary part of the coupling within the antenna circuit, or the switch can be closed so that the two patches are coupled by the conductive pathway and the body tissue has minimal impact since it is only within the antenna circuit in "parallel" with the conductive pathway. It will be appreciated that by this approach, and the use of two patch antennas with a spacing between, it becomes possible to create a significant change in backscattering properties with minimal use of power at the implant device.

The antenna of the first aspect is a non-self-resonant antenna. In this context self-resonance means that the antenna structure and geometry is designed in a way to provide resonance (as used in common antenna methodology). With non-self-resonance (such as an electrode antenna) the antenna itself has no resonance but the impedance of the medium around the antenna can provide the resonance. Resonance may be unnecessary for operation of the non-self-resonant antenna, and instead the operation of the antenna may be based on impedance changes. In example embodiments, when we use the non-self-resonant antenna is used in a conductive medium comprising biological tissues then a current path may be generated between two electrodes of the antenna inside the conductive medium. The current path extends to the biological environment and generates a larger area with a current distribution in the biological medium. The size of the area is much larger than the physical size of the antenna. This give rise to a large virtual size for the antenna and thus high efficiency is achieved. In prior art using a self-resonant antenna, the antenna efficiency is limited to the physical size of the antenna geometry, whereas with a non-self-resonant antenna such as in the first aspect the antenna efficiency can be increased using the larger virtual size of the antenna.

The non-self-resonant antenna and the electrical switch(es) advantageously make use of the impedance of body tissue to affect the backscattering properties of the non-self-resonant antenna, with a two-part antenna having two electrodes arranged to be spaced apart and in contact with the body tissue when in use. The spacing between the electrodes may for example be from 5 mm to 35 mm.

The non-self-resonant antenna uses two conductive patches as electrodes that may form the main components of the non-self-resonant antenna. Metal patches may be used. The two electrodes can be arranged to be in contact with the body tissue, such as via direct tissue contact with the conductive material of the patches, or with an intervening layer of a thin bio-compatible non-conductive coating, such as a polymer coating. The layer of bio-compatible non-conductive material can allow for a gap in the coupling of the antennas to the body tissue, which can enhance operation of the antenna. The layer may be provided via a housing such as a shell placed around the antenna and other parts of the implant device. The housing or coating may encapsulate the implant device and serve to seal it to prevent the internal parts from direct exposure to body tissues and body fluids. This can also enhance the safety of the device and/or reduce the need for bio-compatible materials for the remainder of the device. The layer may for example have a thickness of 1 mm or less, such as a thickness of about 0.5 mm. In some examples a coating with a thickness of 0.1 mm or less may be used.

The backscattering properties of the non-self-resonant antenna are controlled by an electrical switch that is arranged to change the impedance of the non-self-resonant antenna by switching between coupling the two electrodes via the biological medium (e.g. body tissue) and coupling the two electrodes via a conductive pathway. Thus, in effect when the switch is open then a high impedance is provided due to coupling via the biological tissue, and when the switch is closed a low (nominally zero) impedance is provided via the conductive pathway through the switch. The large variation of the impedance can be identified by a receiving antenna placed on the body surface or under the skin. High efficiency of the reflections is achieved due to the large RCS, large bandwidth of the device and large impedance variations. This can generate a large reading range at depths up to 18 cm with a low/moderate transmitter power. High data rates of 12 Mbps have been measured and it is expected that a potential of 70 Mbps can be achieved.

The example antenna uses two conductive patches providing two electrodes of the antenna and these patches are selectively coupled via a switch. The conductive patches may take various forms. They may be considered as patch antennas and hence as distinct from other antennas such as coil antennas or loop antennas.

The conductive patches may in one simple example be patches arranged for attachment to body tissue, whereby the attachment to the body tissue serves to fix the patches with a spacing between them. The switch may then connect or disconnect a conductive pathway between the patches so that the impedance of the body tissue has a lesser or greater effect on the effective impedance of the antenna.

The conductive patches may be spaced apart by virtue of their mounting to a part of the implant, such as a body or a housing of the implant, with the two patches at different points along a length of the implant. In some examples the implant has a tubular form, such as a cylindrical tube or a tube of any other prismatic shape, and the two conductive patches are mounted to the tube and spaced apart along the length of the tube. A tube is a convenient form for implant devices with various purposes, such as for capsule endoscopy.

One or both conductive patches may have a generally two dimensional form such as a rectangle or a disc. One or both conductive patches may have a three dimensional form such as a tube, a section of a sphere (e.g. a hemisphere) or some other three dimensional surface shape such as a surface of rotation of a curve.

In one example the implant device comprises two tube shaped conductive patches, which may advantageously be placed on a tube of the implant, such as a tubular body of the implant. In another example the implant device comprises one tube shaped conductive patch and one patch with a differing shape, such as a disc or a non-tubular three dimensional form (e.g. a section of a sphere, for example a hemisphere). With this arrangement the tube conductive patch and the non-tube conductive patch may be placed on a tube of the implant, for example with a disc on a flat end of the tube, or a hemisphere or other three dimensional form on a rounded end of the tube.

The conductive patches may take the form of tubes of conductive material, such as cylindrical tubes or rings. It is straightforward to manufacture and handle such tubes, and they can readily be inserted into body tissue in various ways. In addition, it is easy to place two conductive tubes (or rings) on a larger non-conductive tube in order to achieve the required distance between the tubes within the body as well as allowing for space to house the switching components and potentially also other elements of the implant device. The same approach can be used with two conductive patches of other shape mounted on a tube, as discussed above. In example embodiments the distance between the two conductive patches (e.g. the distance between two tubes) is limited to be 50 mm or below, optionally 35 mm or below. The distance between the conductive tubes may be at least 5 mm, and it may be in the range 5-35 mm as noted above. Cylindrical tubes such as rings may be used. The cylindrical tubes may have a diameter of at least 3 mm, optionally at least 4 mm, and in some examples a diameter in the range 3 mm to 15 mm. The conductive tubes may have a length along their axis of at least 1 mm, optionally at least 3 mm, and in some examples in the range 3 mm to 6 mm.

The implant device uses one or more switching devices for controlling the backscattering properties, and these may be low power electrical switching devices such as transistors. For example, Field-effect transistors (FET)s such as CMOS FETs may be used. In one example the transistor is a CMOS MMIC device that advantageously can operate with ultra low power. The use of a transistor provides a low power way to alter the backscatter properties of the antenna.

An internal power source of the implant device may be used to control the electrical switch(es) as well as also powering the data source. This internal power source may be a battery or optionally it may be a wireless power transfer system that can use the same antenna as the antenna used for backscatter communications. The implant device preferably does not take power from the antenna during the backscattered communication, which ensures that the antenna can be optimised for maximum reflection and hence maximum range for the backscatter communications with the external communication systems. In fact a cycle of the data (0 or 1) can be used for power harvesting and the other cycle for data transmission.

There may be multiple electrical switches and filters having differing effects on the antenna's backscattering properties and hence allowing for more than two different states for the backscattered signal. This can allow for more complicated data transfer and higher data rates. The method becomes similar to frequency division multiplexing (FDM) for multiband data communication by shrinking high data rate in multiple frequencies. In addition, the switch and filter combination can separate the path for wireless power transfer and data transfer. For multiple frequency usage, the external device should transmit in the multiple frequencies of interest.

The implant device is preferably a medical implant device and it may include sensors for gathering data for medical use, such as use in medical diagnostic methods or for medical research. The sensors are preferably connected to the data source in order to provide information used to generate the data that is transmitted from the data source to the external communication system. The implant device may additionally include additional data processing devices such as a computer processor and/or a memory for data storage.

As noted above it has been proposed in the prior art to combine backscatter communications with wireless power transfer. Using wireless power transfer reduces the range for backscatter within the body since the antenna must necessarily absorb some of and often a major part of the transmitted energy. With the present antenna the design of the antenna in the backscatter communication configuration is for maximum reflection and hence minimal absorption of energy, and the implant device is preferably arranged to use as much as possible of the energy incident on the antenna for backscatter communications. The implant device may be arranged such that there is no wireless power transfer during communication of data via the antenna. Optionally there is never any wireless power transfer, although in some instances there may be a separate use of wireless power transfer when backscatter communication is not being carried out.

The data source or sensors of the implant may have their own battery or a separate wireless power transfer system. The data source may be arranged to provide a data signal for controlling the backscattering properties of the antenna to thereby transmit data from the data source to the external communication system. Preferably this is a low power data signal thereby ensuring maximum lifetime for the implant device. By minimising the power requirement at the implant device the lifespan of the device is maximised whilst also allowing for a high data rate of the backscatter communications.

The implant device may be used to communicate with a second implant device, and thus there may be transfer of data between the first implant device and the second implant device, with the second implant device advantageously transmitting an electromagnetic wave toward the implant device, and being arranged to receive a backscattered signal from the implant device.

Alternatively or additionally the implant device may be provided in combination with an external communication system that interacts with the implant device to receive data from the implant device. For example, this may be in the context of a system for gathering medical data about a patient.

The external communication system can be arranged to transmit an electromagnetic wave toward the implant device, and to receive a backscattered signal from the implant device. This may be done using a single antenna acting as both transmitter and receiver, but preferably the external communication system includes separate transmitting and receiving antenna. One reason for using multiple antennas is to reduce the coupling between the transmission antennas and receiving antennas in order to prevent the receiver saturation. This allows the receiver to operate in its full dynamic range for receiving the relatively weak backscatter signals. In addition, in case of multipath propagation, using bi-static (dual antennas) or multi-static (multiple antennas) performs better than mono-static (single antenna) configurations as this removes the probability of deep signal fading.

The electromagnetic wave may be a radio wave and in particular may be at a frequency designated for use with medical implants. Such frequencies are selected based on their availability and loss characteristics in living tissues. The Industrial, Scientific and Medical (ISM) frequency band, and Medical Implant Communication Service (MICS) at 400, 600, 800 and 1400 MHz are used for wireless communication with medical implants and the external communication system may hence use one of these frequencies. Due to the behaviour of the non-self-resonant antenna then any frequency from DC to 1500 MHz is expected to allow for communication from the implant to the external communication system.

The transmitter may comprise an on body antenna as the transmitter antenna, This may be an arrangement of any efficient radiator toward the implant device. There may be multiple transmitting antennas at multiple locations acting together in order to transmit the electromagnetic wave toward the implant device. The use of multiple antennas at different locations can allow the signal strength at the implant device to be maximised whilst avoiding excessive levels of electromagnetic radiation at the body surface, thus increasing the potential range for the backscatter communications without exceeding limits on the exposure of the patient to radiation. In addition, the multiple antennas on the body surface can be placed in orthogonal configurations to implement the polarization diversity, thus the received signal is less dependent on the implant orientation. This is mandatory for applications such as capsule endoscopy in which the capsule is moving in the digestive tract and it may have different orientations relative to the external antenna.

The transmitting antenna(s) may be placed directly on the body with a separation gap to prevent direct contact to the skin. Alternatively, or additionally, a matching layer may be placed between the antenna(s) and the skin. The matching layer may comprise a low loss dielectric material, for example water or an aqua based dielectric material. With the use of a matching layer the body Specific Absorption Rate (SAR) is reduced and heat generated due to the radiation can be dissipated.

In some implementations, the external communications system may be arranged to reduce the amount of the coupled power at the receiver antenna due to the transmitter antenna by using multiple transmitter antennas to make a null coupled signal at the receiver. This means that even a very weak backscatter signal can be recovered at receiver.

The invention further extends to the use of an implant device as in the first aspect, for example in order to gather medical information about a patient or to treat the patient. The implant device may include any of the other features discussed above.

The use of the implant device may comprise: implanting or inserting the implant device into the patient; transmitting an electromagnetic wave toward the device from an external communication system that is outside of the body; controlling the backscattering properties of the antenna in order to thereby transmit data from the data source using the backscattered signal from the antenna; and receiving the backscattered signal at the external communications system.

Optionally, the use of the device may include using the implant device to gather medical information at one or more locations within the patient's body, and then transmitting this information out of the body via the backscatter communications with the external communication system. The use of the device may further include controlling the backscatter properties of the antenna to transmit data via the backscatter signal by means of switches as described above.

Certain preferred embodiments of the present invention will now be described by way of example only and with reference to the accompanying drawings, in which:

FIG. 1 is a plot of conductivity versus frequency for some biological tissues;

FIG. 2 shows an arrangement for galvanic electrodes as a non-self-resonant antenna;

FIG. 3 is a circuit model representing the operation of the switch in FIG. 2;

Figure 10:
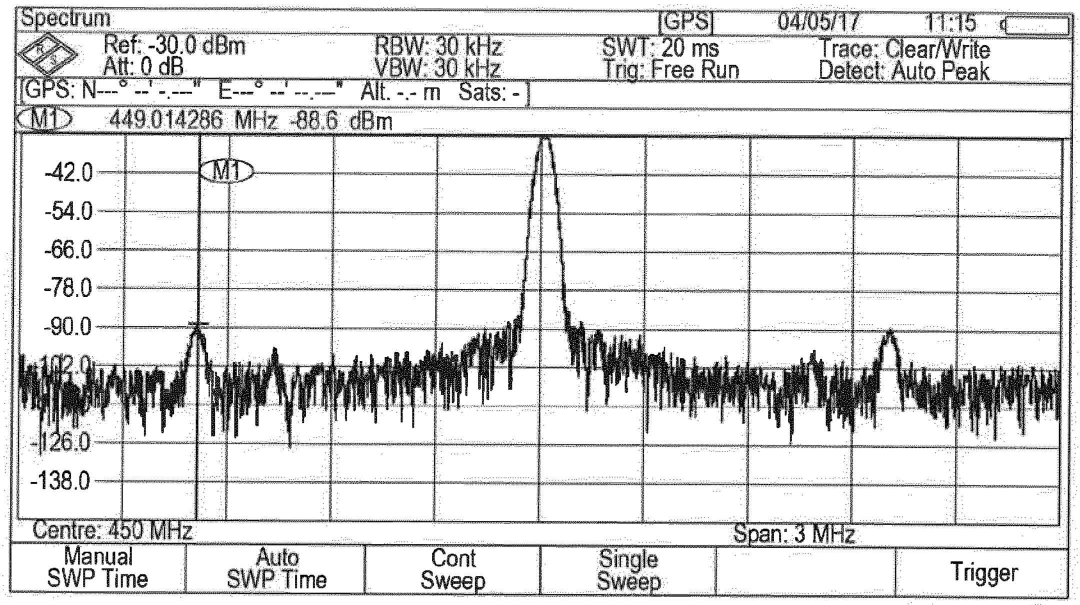

FIG. 10 shows the spectrum analyser measurements for a similar test with the implant capsule at a depth of 17 cm The preferred embodiments relate to an implant device with a non-self-resonant antenna for backscatter communications as well as to an external communication system for receiving data from the implant device. The implant device gives rise to a new technique of wireless backscatter data connectivity for the medical implant communications. The proposed human body backscatter communication (HBBC) is appropriate for the conductive mediums, in which the regular backscatter communication and RFID techniques are hindered due to the tissues' loss and the implant antenna performance degradation. Similar to the backscatter techniques, our approach removes the transmitter from the implant device that can save the power consumption of the implant and physical space. A remote reader is used to transmit RF energy and read the information signal which is modulated by the implant's data source. Using this approach, the implant power consumption for communication reduces from several m-watt to some nano-watt thanks to using a switch circuit instead of a full transmitter chain in a conventional wireless communication. Thus high data rate and long-life connectivity are guaranteed with small implant devices.

Our unique technology is based on the non-resonating antenna which performs effectively in the conductive mediums. The non-resonating antennas can provide ultra-high efficiency in the conductive mediums and ultra-wideband performance compared to the resonating antennas. Thus the link budget with the non-resonating antennas performs significantly better than the resonance base antennas. We implement the impedance of the media around the antenna for the antenna impedance tuning, and with the backscatter method the media's impedance is altered using the implant data signal and switch.

A reliable data connectivity with low to high rates (potential up to 70 Mbps) for the implant depths beyond 18 cm becomes feasible with a moderate transmitter power level (less than 100 m watts) of the remote reader. Therefore the system can be implemented for high depths connectivity. The implant size in our new approach can be reduced to 5 mm and it can be less (1 mm) for short distances. The method can be used for the implant to implant or implant to external body communication scenarios with potential applications in wireless cardiac pacemakers, wireless capsule endoscopy (WCE) and in-body wireless sensor network.

The regular wireless backscatter communication and RFID techniques are used in free space in which a remote reader transmits EM wave, and the received signal with a resonance antenna structure of a tag device is modulated and the signal is re-transmitted in the wave propagation channel. A switch circuit in the tag device performs the signal modulation. The remote reader demodulates the wave reflections for data detection. Operating at the tag resonance is essential to increase the antenna radar cross section (RCS) and provide appropriate backscatter link budget. The size of the tag antenna plays a crucial role on the system's performance, and by reducing the electrical size of the antenna from the resonance length ($\lambda/4$) the efficiency of the scheme is degraded.

Using the conventional backscatter and RFID methods are feasible for superficial medical implant communications for the sensing purpose. In this application, the communication range is small (1-3 cm), and the data rate is limited to some kbps. The main limitation is the implant size that should be low (<30 mm) and the frequency dependent loss of the biological tissues that increases with frequency. This imposes using the MHz frequency range (<1500 MHz). Therefore, the normalised antenna size becomes small ($<\lambda/10$) causing the antenna efficiency reduction. Furthermore, due to the small size, the antenna reactive field (near field) becomes significantly strong that is absorbed by the antenna surrounding tissues and give rise to the specific absorption rate (SAR) that reduces further the total antenna efficiency. These inherent limitations with the resonant antennas limit the application of RFID for biomedical implant communication.

Using antennas with large RCS and tuning the implant antenna resonance can help on increasing the communication range of the implant device. However, due to the small efficiency of an implanted antenna and the limitations on the applied reader's power (due to RF absorption and SAR) the communication range in earlier work with resonant antennas has been limited to about 8 cm with an applied power of 100 m watts. Also, the resonance frequency of the implant antenna shifts due to different tissues' loading that plays a crucial role in the backscatter performance. A complex system should be used to find the best frequency for the backscatter. Furthermore, the data rate that can be delivered with a small resonating antenna is limited.

The currently proposed approach is based on a backscatter mechanism which is adapted for the conductive or lossy mediums such as the biological environments. We use a non-self-resonant antenna with medium impedance modulation for realising human body backscatter communications (HBBC). The efficiency of the new antenna is not affected by the lossy material similar to the resonance antennas. The non-self-resonant antenna can provide appropriate impedance in the conductive mediums by exploiting the loss of the environment for matching. The antenna should have direct contact with the biological tissues, or it can hold a tiny gap (<0.5 mm) as coating with the surrounding material. As the antenna is a non self-resonance structure, the efficiency is not a factor of the antenna electrical length. Thus the antenna can hold very small size with high efficiency. The near-field of the non-self-resonant antenna is not strong compared to the resonance structures thus the dissipated power around the antenna is significantly low. This introduces small specific absorption rate (SAR). All these features provide a reliable communication link with a remote reader for HBBC application that cannot be achieved with the conventional RFID and self-resonance techniques.

The implant media defines the impedance of the proposed non-self-resonant antenna instead of the antenna structure itself. As the medium impedance can be assumed constant for over 30% of centre frequency, we can define the antenna as frequency independent. The result is that the antenna becomes ultra-wideband and can perform from DC to several GHz frequency ranges. Consequently, the same antenna can be used for galvanic and radiative communications. Also, the potential data rate of the system becomes significantly high due to the available bandwidth with low distortion.

To implement the backscatter modulation using our non-resonating antenna, we alter the impedance between two loci of the implant electrodes in the medium through an internal switch mechanism. Thus, we can use the impedance of the environment and modulate it. Therefore, efficient backscatter performance is achieved. The backscatter device is ultra-wideband, and thus a wide range of frequencies (DC-1500 MHz) can be used for data communications in the biological tissues. Also, due to the available wideband feature, we can transmit very high data rate (70 Mbps at 450 MHz centre frequency). We note that the operation in all the frequency range is not similar and is not optimal. The operation mainly depends on the separation between the two electrodes of the antenna. Small separation imposes better operation at higher frequencies.

The proposed design is used for communications from implant to implant or from implant to an on-body receiver with applications for wireless pacemakers and wireless capsule endoscopy (WCE). The disclosure herein provides the design and measurement results of the technology above. We describe the design concept of the new HBBC device, and the arrangement of the reader's antenna together with the system implementation. The measurements are conducted to provide the optimum frequency for HBBC, the effects of the device size and communication depths are measured.

The HBBC is presented for two possible scenarios:

- Implant to implant communications for frequencies below 30 MHz with galvanic communications.
- Implant to on-body communications based on the radiative coupling for frequencies above 70 MHz.

Using backscatter for implant devices requires compact size implementation less than 35 mm. The frequency range that the biological tissues indicate small conductivity values (less loss) are below 1500 MHz (see FIG. 1 for a plot of conductivity versus frequency for some biological tissues). Therefore, the electrical size of an implanted antenna becomes less than $\lambda/10$ that is in the categories for the small antennas. The small antennas indicate strong near-field with high Q-factor and narrow bandwidth. Loading a small antenna with the lossy biological tissues such as the implant scenarios, dissipates most of the evanescent waves to the antenna surrounding tissues and thus reduces the antenna efficiency and the Q-factor drops. Therefore, using resonance antenna structure becomes problematic for the medical implant applications. This is the inherent character of any small antenna in the implant applications and indicates low efficiency.

FIGS. 2 and 3 show a design considered for biological conductive mediums, in particular for backscatter communications. The antenna 12 includes two metallic electrodes 16 with a small distance between the electrodes 16. A remote reader 18 receives signals from the antenna 12 via backscatter communications. The antenna 12 in free space shows an infinite impedance between the two electrodes 16. However, if the antenna immersed in a conductive medium, the device impedance is specified by the material characteristics between the two electrodes 16 and the separation of the electrodes 16. A gap between the electrodes 16 and the body tissue can also have an impact, such as the gap 22 provided by the optional shell 24 discussed below in relation to FIGS. 4B, 4C and 4D. Also, as the material for the biological tissues is frequency dependent the impedance between the electrodes 16 also becomes frequency dependent. The curves in FIG. 1 show that the conductivity can be considered as almost flat for about 30% of bandwidth at frequencies below 500 MHz. The proposed antenna 12 with two electrodes 16 can be used as an active transmitter or receiver for a broad range of frequencies (DC-1000 MHZ) with appropriate impedance matching. The antenna impedance for a capsule size larger than 5 mm is in a range that can be tuned effectively for wideband usage. The main problem with using the antenna as a direct transmitter is the resistance between the two electrodes 16, and this can be small depending on the tissues between the electrodes 16. The low resistance drains the transmitter's power and reduces the transmitter efficiency.

For the backscatter purpose, a wire connection between the antenna electrodes 16 with a switch circuit 14 between both electrodes 16 is used. By controlling the switch operation, the impedance of the medium between the two electrodes 16 can be modulated between zero ohms (for the switch on) and the medium's impedance (for switch off) defined by the conductivity (a S/m) of the media and the separation between the electrodes 16. By reducing the conductivity (for example at fat tissues) the impedance between the electrodes 16 increases and with high conductive tissues (blood, muscle) the impedance reduces. Thus the antenna is easy to implement at lossy mediums in contrast to a resonating antenna. Therefore, if a remote reader provides a voltage difference in the medium between the two electrodes 16, the switching alters the current in the equivalent circuit that can be retrieved by the reader. Controlling the switch 14 with the implant data source expresses the signal modulation at the reader's side 18. As can be seen, the environment impedance switching is the basis for our backscatter communications and not the device self-impedance. Therefore, any signal and frequency that can provide an appropriate voltage difference between the two electrodes 16 can be used for the sensing purpose.

The electrodes 16 can be provided by cylindrical tubes (or rings) of conductive material which are shown in side view in FIG. 2, with the dimension W being a length/width of the tube along the axis of the cylinder and the dimension D being a diameter of the tubes. The dimension L shows the spacing between the two electrodes 16. We propose the distance between the electrodes 16 of range (5 mm<L<35 mm) for optimum link performance for all frequency range from DC-1000 MHz and the diameter of the electrodes 16 is proposed for (D>4 mm) and the strip width (tube length) of (W>1 mm). However, we can use smaller size L, D and W with some loss in the system performance.

FIGS. 4A to 4E show various arrangements for the implant device and in particular for the conductive patches providing electrodes of the antenna. These implant devices may be manufactured for HBBC measurement.

Figure 4A:
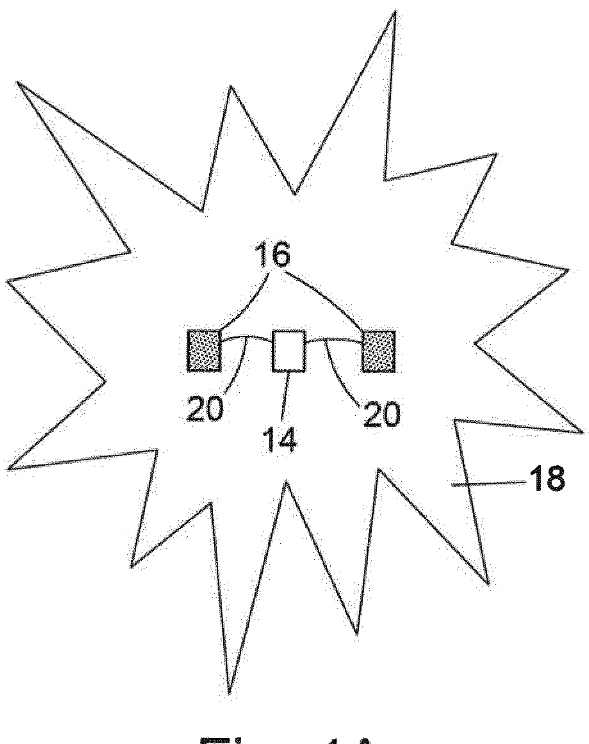
FIGS. 4A to 4E show various arrangements for the implant device and in particular for the conductive patches providing electrodes of the antenna.

FIG. 4A shows the use of two conductive patches 16 for the antenna electrodes, with these patches being attached to body tissue 18. The switch circuit 14 is connected to the two patches 16 via wires 20. The attachment of the patches to the body tissue 18 is used to fix them at the required spacing.

The examples of FIGS. 4B to 4E differ from that of 4A in that a body of the implant device 12 is used to support the patches 16 and hence to provide spacing between the patches. The implant device 12 in these examples has a tubular form, which is shown in cross-section. The switch circuit 14 as well as the conductive pathway (20, not shown) is within the body of the implant device 12. The patches 16 forming electrodes of the antenna are placed at an outer part of the implant device 12.

Figure 4B:
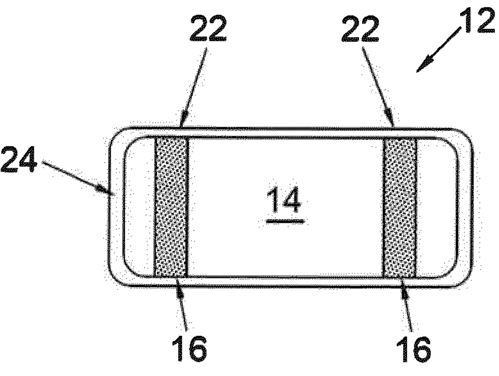
Figure 4C:
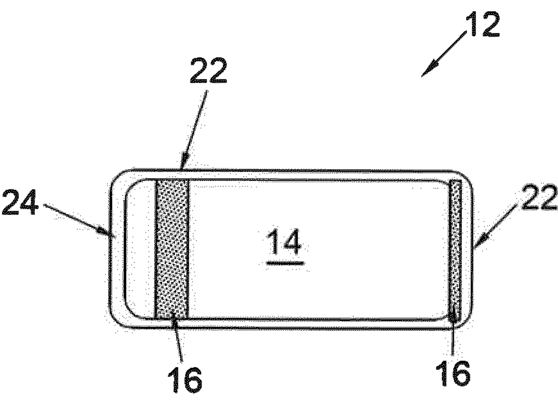
Figure 4D:
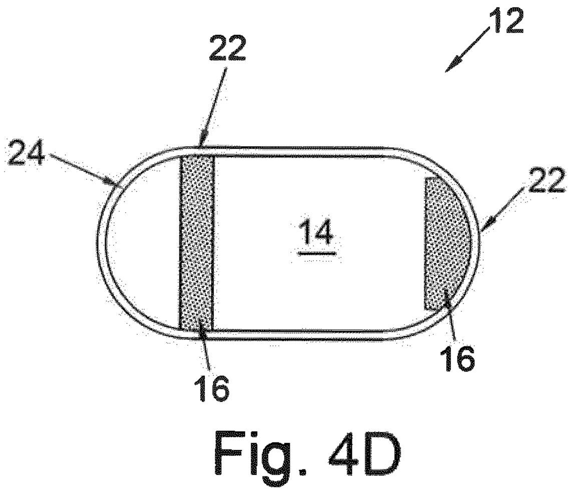

In FIG. 4B the patches 16 take the form of two tubes at two ends of the implant device 12. In FIG. 4C the implant device 12 uses one tube shaped patch 16 and one disc-shaped patch 16. The disc-shaped patch 16 is at an end of the tubular form of the implant device. The example of FIG. 4D uses rounded ends for the implant device 12 and one of the patches 16 is a tube, whilst the other patch 16 is a curved surface fitted to one of the rounded ends. For example, this may be a section of a sphere. Optionally there is a gap 22 between the patches 16 (i.e. the electrodes) and the body tissue, with this gap 22 being provided by an outer shell 24. The gap 22 operates as a capacitive element. The use of a gap 22 in this way may be done for backscatter applications at high frequencies (e.g. above 70 MHz).

The implant device 12 might include a camera (not shown) or other sensors. With the use of a camera this could be placed at an end of the device where there is no patch 16, such as the left hand end of the implant device 12 of FIG. 4D.

Figure 4E:
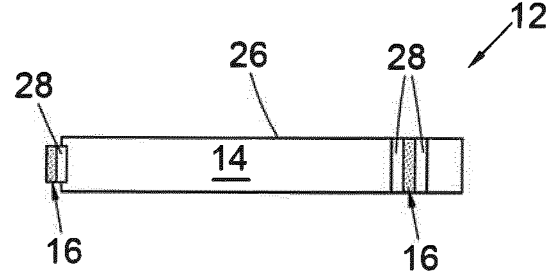

For some applications it may be useful to have a conductive outer shell 26, as shown in FIG. 4E. In this case the two patches 16, which may be a disc-shaped patch 16 at one end and a tube-shaped patch 16 at the other end, should be shielded from the conductive outer shell 26 by insulating material 28. Relevant applications include those in which using the metal is required for reasons of biocompatibility and/or long life of the implant device 12. An example of this is for leadless cardiac pacemakers. The backscatter electrodes 16 should be isolated in RF (reader frequency) from the casing. The electrodes 16 can be in contact with the surrounded medium or with a coupling gap.

In the experiments to validate the proposed concept different implant capsules have been manufactured and measured inside body phantom filled with phantom material (for example saline 4%) for simulating the human body tissues. A water container of 50×30×30 $cm^3$ was used as our test phantom and filled with the fluid. The on-body antennas were placed on the container's surface. The capsule antenna 12, by way of example using an antenna configuration as shown in FIG. 4B, was immersed in the liquid in front of the reader antennas and parallel with the reader's antenna surface. A wide range of view angles in front of the reader antennas can provide data connectivity with the implant capsule 12. To cover whole areas for the scenarios with unknown locations and orientations of the capsule device 12, multi-antenna usage is proposed with a selection mechanism for providing the connectivity. The measurements have been validated for the in-vivo animal experiments confirming similar performance as the liquid homogeneous phantom.

Figure 5:
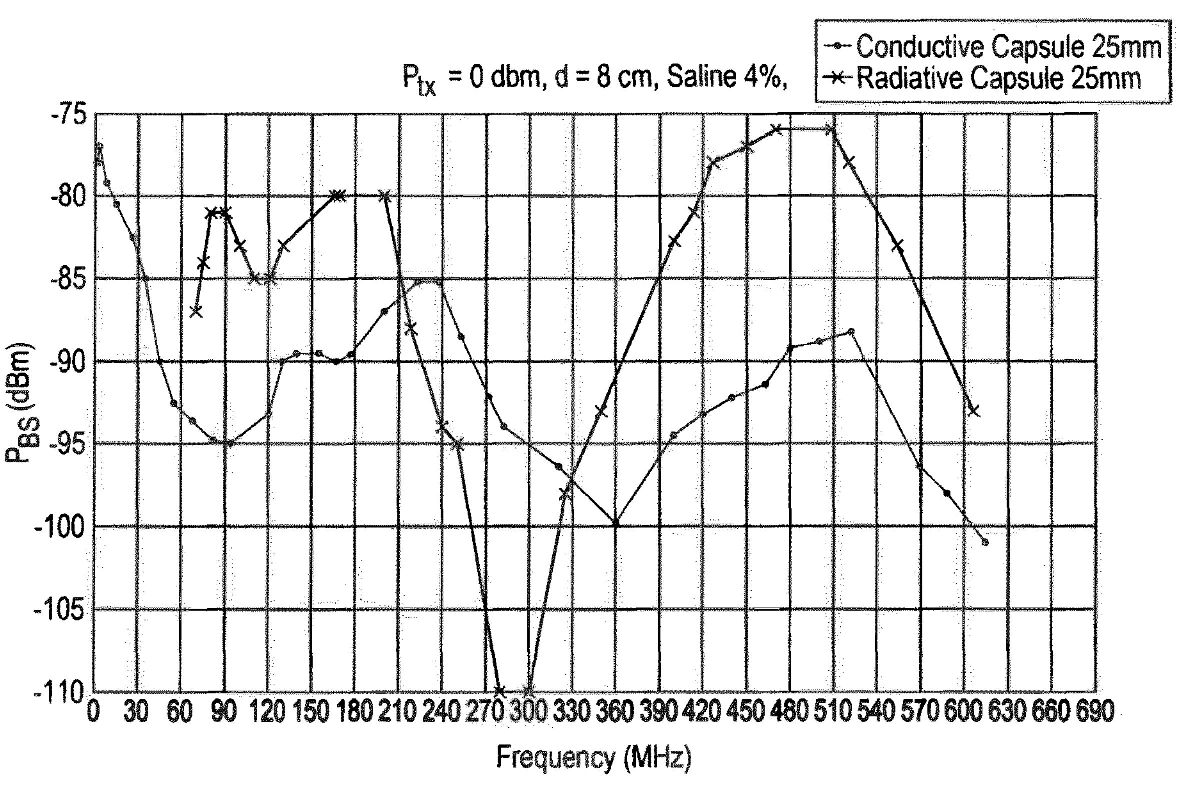
FIG. 5 shows test results with backscatter signal level plotted against frequency.

In the first measurement setup, we define the frequency range which is appropriate for HBBC application. We consider two different scenarios with a conductive and radiative link. In the radiative link, the on-body antenna is placed with a gap to the container's surface. The source power is 0 dBm (1 m watt) and the backscatter signal level is recorded for the capsule at depth=80 mm. A capsule size of 25 mm is used in the measurement process. FIG. 5 shows the backscatter signal level versus frequency. As shown, the frequency range of 420-550 MHz shows high backscatter signal level. Other frequencies at 90 and 180 MHz provides good signal level. For the frequencies at 300 MHz band the signal level drops. Here we are interested in the MICS and RFID frequency bands at 402 MHz and 450 MHz. We note that the transmitted signal is not modulated thus the regulations for the un-modulated signal is applied to our system. The received signal is modulated and has wideband property, but the signal level is less than −85 dBm. As the modulated signal level is too small, it can be accepted by the regulatory standards for transmission. For instance, UWB transmission with a signal level below −80 dBm is an unlicensed band. Therefore, there is not any bandwidth limitation with the reflected signals which are feeble.

In the second measurement for HBBC, the same scenario with the reader antennas inside the liquid phantom is measured. The reader antennas are in direct contact with the medium. As expected, the high-frequency components are attenuated due to the direct contact with the lossy medium. However, the low-frequency band (galvanic coupling) is dominant for the frequencies below 30 MHZ in which the backscatter signal is significant. Therefore, the galvanic part is useful for low frequencies. The available bandwidth is limited in the lower frequencies. The bandwidth would be enough for HBBC connectivity with low rate requirements about 30% of the transmitter frequency. The same set-up can be used for high data rate connectivity with transmitting at low frequency and receiving the backscatter signal at a higher frequency (upconverted reflections). For example, by transmitting in some kHz in the forward path, we can modulate the backscatter signal at a higher subcarrier rate (1-10 MHZ) in the backwards path to obtain larger bandwidth for the data. In this case, the reader in TX and RX has different frequencies. This method would be appropriate for wireless pacemaker usage. Also, we can consider galvanic coupling for the forward path and the radiation for the backwards path. By using this communication style, the transmitted signal is in kHz and the reflected signal is at high frequency (MICS frequency band). The requirement is that a fast switching at the backwards frequency must be operated.

Figure 6:
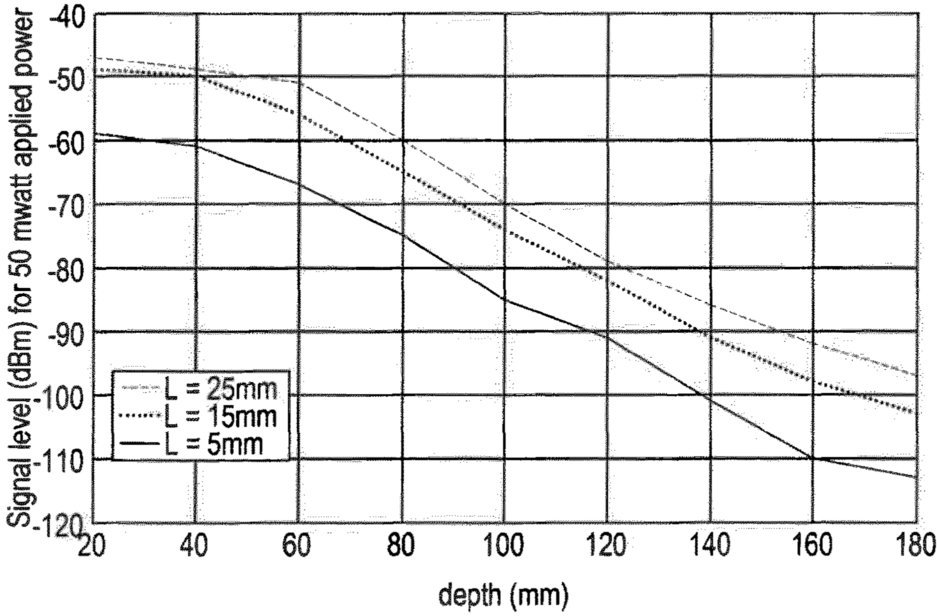
FIG. 6 shows the backscatter signal level versus depth for different capsule sizes 25, 15 and 5 mm at 455 MHz.

Considering the frequency range of 420-550 MHz for the radiative HBBC, we have measured data connectivity with different capsule sizes. In this measurement scenario, SDR is used as the transmitter and receiver device. We applied a power level of 50 m watt to measure the connectivity within depth, and the backscatter signal quality is recorded. FIG. 6 shows the backscatter signal level versus depth for different capsule sizes 25, 15 and 5 mm at 455 MHz. The capsule of size 25 mm performs better than the smaller capsules because of the available higher induced voltage at the electrode ends and the larger differential RCS provided by the impedance switching. The capsule with 5 mm size performs about 15 dB worse than the 25 mm capsule. Increasing the capsule size for more than 25 mm will not increase the backscatter signal significantly. This finding indicates that we can reduce the capsule size to 5 mm or less depend on the applicable depth. The backscatter path loss at 455 MHz band is about 5 dB/cm for all capsules. The loss decay is smaller at close distances to the reader due to the available near field of the reader.

Using the applied power of 50 mwatt, we can provide a depth connectivity up to 18 cm with signal level of −95 dBm. The capsule with 5 mm size can operate to depths of around 13 cm. The data rate for these systems is around 12 Mbps. The system can provide high data rate up to 70 Mbps in a single channel with small distortion. Frequency division multiplexing (FDM) can be used for an improved receiver performance.

Operating at 650 MHz can provide an increased link performance by 10 dB for the small capsule of size 5 mm. Therefore we should make a tradeoff between frequency and size of the implant capsule. Small size capsules provides improved backscatter at high frequencies. The measurements have been conducted in in-vivo animal experiments using a pig under general anesthesia. High data rate connectivity is illustrated for in-depth (12-18 cm) applications in the abdomen and chest of the animal for wireless capsule endoscopy and wireless pacemaker applications.

The measurement of backscatter with the galvanic capsule shows that the signal loss for one-way connectivity is maximum 1.5 dB/cm and is 2.5 dB/cm for the radiative links. The efficiency of the coupling between the on-body and capsule antenna for capsule size of 25 mm is −10 dB. The coupling with complete matching provides a link with 30 dB loss at 8 cm. This means by transmitting 100 m watt, the received power at the capsule is 100 microwatt. Considering an efficiency of 35% for a rectifiers circuit we can deliver 35 microwatt power to the implant at 400 MHz frequency band. We expect more power transfer for the conductive scenarios using the non-resonating antenna, as the loss is smaller in the lower frequencies by about 8 dB for 8 cm. Therefore the proposed non-self-resonant antenna 12 can be used for WPT.

Figure 7:
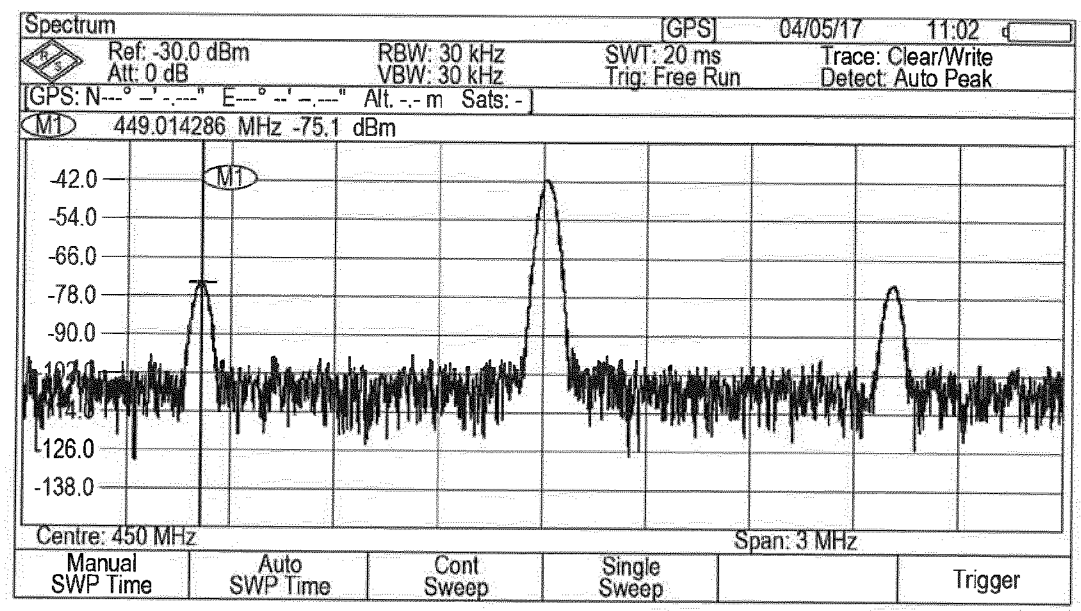
FIG. 7 shows a backscatter signal at a spectrum analyser for a test of a transmitted period signal with implant capsule at depth 9 cm.
Figure 8:
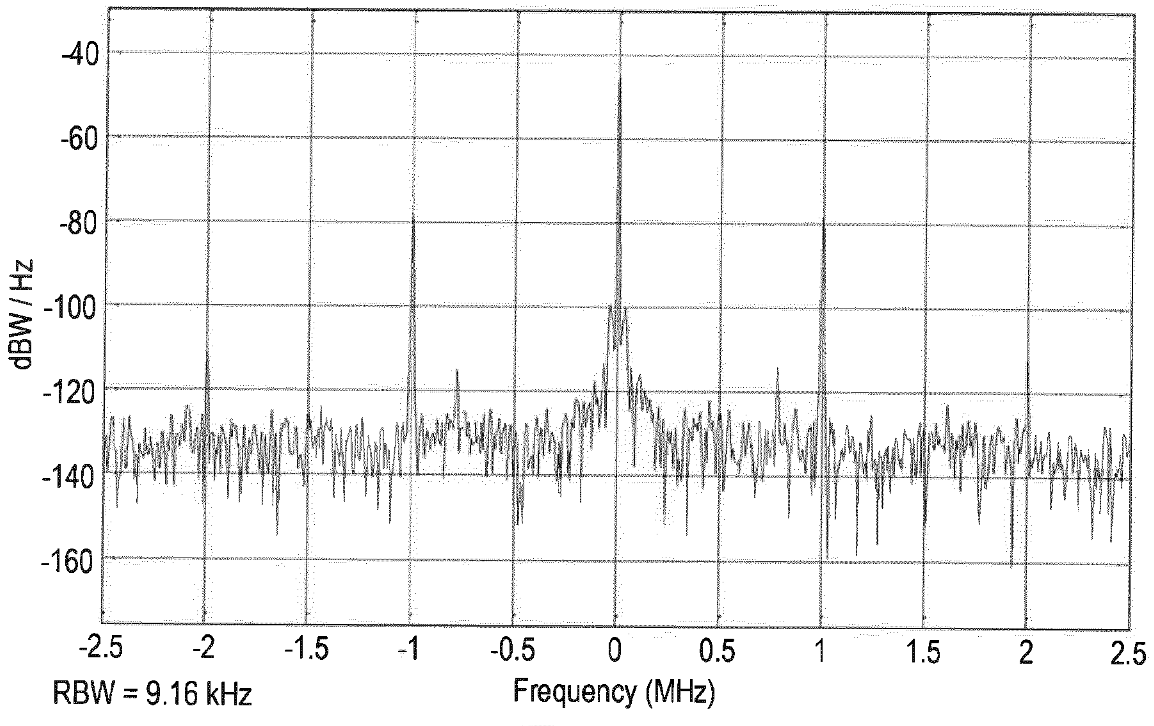
FIG. 8 shows USRP spectrum analyser measurements for the same test.
Figure 9:
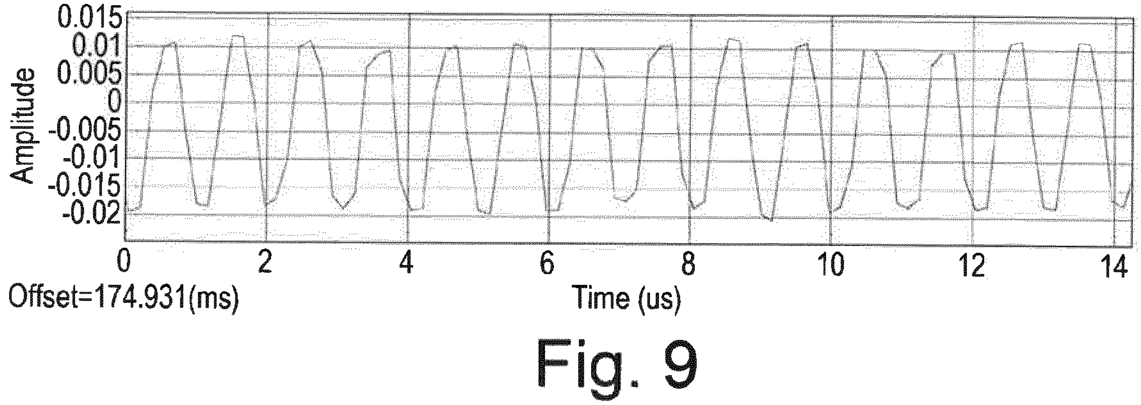
FIG. 9 shows the decoded data signal from the test of FIG. 8.

In another example, measurements were taken with SDR at 450 MHz band. USRP N210 was used as the reader system, the TX frequency was set to 450 MHz and the power is 0 dBm. A capsule size (L) of 25 mm was used at 9 cm depth, and the capsule was switched at 1 Mbps. The backscatter signal at the spectrum analyser was measured as shown in FIG. 7. Similarly, the spectrum was measured on USRP spectrum analyser and this is shown in FIG. 8, and the data signal is decoded as shown in FIG. 9.

The measurements were also conducted for a depth of 17 cm with increasing TX power to 15 dBm (30 mwatt) and RX gain of 15 dB in which we can detect the data signal of 1 Mbps. Based on the USRP bandwidth of 20 MHz the same performance can be achieved for data rate up to 10 Mbps. The spectrum for depth 17 cm is shown in FIG. 10 with the BS level −88.6 dBm.

The relative rotation of the reader antenna and capsule antenna 12 can cause signal degradation due to the polarisation mismatch. For a relative polarisation angle of 45 degrees, the signal loss is 5 dB and is increased to 10 dB for 60 degrees of relative rotation. The signal further reduces for rotation angles above 60 degrees. Therefore, the arrangement of the reader antennas should be adjusted to compensate for the relative rotation by multi-antenna configuration.

An implantable device is proposed that is adapted for conductive mediums and that allows for effective backscatter communications with low power usage. The introduced antenna 12 is a non-self-resonant structure with two conductive electrodes 16 that makes use of the impedance of body tissue during the antenna operation. As the antenna 12 is a non-resonating device, the losses associated with the near field, in the small resonating antennas, is not a limiting factor. The non-self-resonant antenna 12 is frequency independent with very wide range of stable impedances with frequency. Therefore, ultra wideband performance with the antenna 12 can be obtained. For the backscatter operation, a switch mechanism 14 is used to alter the system impedance between the two electrodes 16. The modulation of the medium impedance is used to express the data and backscatter connectivity. The proposed system can offer very high data rate connectivity of 70 Mbps at 450 MHz centre frequency for depths beyond 18 cm. The system is tested with different capsule sizes of 5, 15, 25 mm and data connectivity up to 12 Mbps to depths 12-18 cm are demonstrated with 50 m watt of the applied power. Depending on the usage and application scenarios, the frequency ranges from DC to 1500 MHz can be used for the backscatter connectivity. The power consumption of the implant device reduces from m-watt to several nano-watts thanks to using a switchboard instead of a complete transmitter in the implant. The technology is appropriate for WCE and pacemaker or implant wireless sensors network connectivity.

The proposed technique can also provide analogue data connectivity for the implant device in case that a varactor diode is used as the switch instead of the switch circuit 14. The reason is that we use the medium impedance modulation and not the antenna impedance that can reduce the RCS of the antenna.

Therefore, by using the concept of data transfer with the medium impedance modulation, we can provide data connectivity for very deep implant devices with small applied power to the medium. One reason for this is that the system is not based on an antenna resonance in which the tissue loading diminishes the high Q value of a small antenna. Also, all the frequency range from DC to several GHz can be covered for the backscatter data transfer. Any method that can provide a voltage difference between the two electrodes 16 of the implant device can be used for the backscatter sensing.

Two frequency ranges are considered for generating the voltage difference between two loci in the conductive medium.

1—Low frequencies (below 30 MHz) in which the electric conduction is the main way of signal transmission in the medium.

2—High frequencies (frequencies above 80 MHz) based on radiation of the RF field into the conductive medium.

For electric conduction direct contact between the electrodes 16 and the conductive medium is essential. However, for radiative coupling, a gap between the reader 20 and the medium is required to induce the electric field in the environment. Also, the implant device in the radiative scenario can hold a spacer or a non-conductive coating. Different frequency bands that can provide high penetration inside the biological tissues and provide a larger voltage difference between the implant electrodes 16 are found through extensive measurements. A summary of the features and findings are as follows:

An implant device using a non-self-resonant antenna 12 with two electrodes 16 can operate for backscatter data connectivity for all frequency range from DC to GHz. The lower band is limited to several tens of kHz to prevent the ionic movements and biological cell damage. The upper band is limited by the material loss of the biological tissues nominally to below 1000 MHz.

- The backscatter method is based on the medium impedance modulation and not the antenna impedance modulation used in the conventional RFID and free space backscatter.
- There is no resonating antenna for the implant radiator. Consequently, the device size and Q-factor are not the criteria for backscatter in conductive mediums.
- The media impedance modulation approach can be integrated into any shape of an implant device such as cylindrical or planar structures. The only requirement is to have enough separation between the electrodes 16 of the implant device to obtain a considerable impedance between electrodes 16.
- The separation between the two electrodes 16 of a device defines the system impedance and performance. The separation depends on the available space of the implant. Lengths between 25-35 mm are optimal. However, it can be reduced to about 15 mm with some loss of performance. Small sizes are possible around 5 mm but operation at higher frequencies is recommended.
- The thickness or diameter of the device is not a critical factor. The electrode surface can be in the order of $mm^2$ (exp. $2\times2$ $mm^2$).
- Two ways of energy transfer to the implant device are considered by using the reader: Galvanic coupling and radiative coupling.
- The optimum frequency band for the galvanic conduction is proposed for the implant to implant communication for frequency range of DC to 30 MHz.
- The galvanic HBBC can be used for the implant to an external device communication if the wave radiation around the body is not permitted.
- The frequency range for radiative coupling is measured in the phantom and optimum frequency of operation is extracted: namely three frequency bands are distinguished: 90, 180 and 450 MHz. We can define the frequency range at 650 MHz for communication with small implants of size 5 mm. Similar results have been confirmed using in-vivo animal experiments.
- For the galvanic method, a conductive contact between external electrodes 16 and the body is required. We can use a conductive gel to provide the connection. In the MHz range, the fatty tissues have less effect on the link performance loss.
- As the implant system is frequency independent device, Ultra wide bandwidth is available for data transmission due to the nature of the backscatter phenomenon. The bandwidth is mainly limited by the backscatter signal amplitude dispersion. This problem can be easily solved by a matched filter. The available bandwidth is more than 70 MHz at the 450 MHz centre frequency for radiative coupling mechanism.
- The transmitter is a single tone signal transmitter and follows the related regulations for the transmitter power. For example, at 450 MHz it can be up to 300 mwatts. The backscatter signal which is modulated is below −80 dBm and can be considered as UWB spectrum in the unlicensed band.
- Using the galvanic method, the bandwidth is limited to about 20% without amplitude dispersion. It can be increased if a matched filter is used.
- Using multi-frequency for multi-capsule implementation is possible by applying an RF filter in the switching path of the implant device.
- Backscatter with a capsule of 25 mm and data rate of 12 Mbps is demonstrated for depth 8 cm and 1 m watt transmitted power. The power rating of 50 m watts can provide connectivity to the depth of 18 cm at the centre frequency of 450 MHz.
- Similar connectivity and depth of communication can be achieved with the galvanic method. However, the data rate is limited due to the limited bandwidth.

The invention claimed is:

1. An implant device for use within a body, the implant device comprising:

a data source; and a non-self-resonant antenna for backscatter communications with an external communication system, the non-self-resonant antenna comprising at least two electrodes including two conductive patches that are arranged to be spaced apart when the implant device is in use;

wherein the implant device is arranged to control backscattering properties of the non-self-resonant antenna in order to thereby transmit data from the data source to the external communication system; and wherein the implant device is arranged such that the backscattering properties of the non-self-resonant antenna are controlled by one or more electrical switches including an electrical switch that is arranged to change an impedance of the non-self-resonant antenna by switching between coupling the at least two electrodes via body tissue and coupling the at least two electrodes via a conductive pathway, wherein coupling the at least two electrodes via the body tissue generates a current distribution between the two electrodes inside the body tissue, the current distribution having a larger area than the physical size of the antenna and thereby acting as an extended virtual antenna, the implant device thereby being configured for data communication rates at tissue depths of at least 8 cm.

2. An implant device as claimed in claim 1, wherein the spacing between the at least two electrodes is in a range of 5 mm to 35 mm.

3. An implant device as claimed in claim 1, further comprising a layer of bio-compatible non-conductive material for providing a gap between the body tissue and the at least two electrodes.

4. An implant device as claimed in claim 3, wherein at least one of the following:

the layer of bio-compatible non-conductive material is provided by a shell around an outside of the implant device; and the layer has a thickness of 1 mm or less.

5. An implant device as claimed in claim 1, wherein at least one of the conductive patches takes a form of a tube of conductive material.

6. An implant device as claimed in claim 5, wherein at least one of the following:

the conductive patches are provided by two conductive tubes on a larger non-conductive tube; and the conductive tubes forming the conductive patches have a diameter in a range of 3 mm to 15 mm and a length along their axis in a range of 3 mm to 6 mm.

7. An implant device as claimed in claim 1, wherein the conductive patches include one or more of a disc-shaped patch, or a patch provided by a section of a spherical surface.

8. An implant device as claimed in claim 1, wherein the backscattering properties of the antenna are controlled by the one or more electrical switches that change a load and/or geometry of the antenna, and wherein the device comprises multiple electrical switches and filters having differing effects on the antenna's backscattering properties and hence allowing for more than two different states for a backscattered signal.

9. An implant device as claimed in claim 1, wherein the implant device is a medical implant device and includes one or more sensors for gathering data for medical use.

10. An implant device as claimed in claim 9, wherein at least one of the following:

the one or more sensors are connected to the data source in order to provide information used to generate the data that is transmitted from the data source to the external communication system; and the data source and/or the one or more sensors of the implant device are powered by a battery or a separate wireless power transfer system.

11. An implant device as claimed in claim 1, wherein at least one of:

the implant device is arranged such that there is no wireless power transfer to the antenna during backscatter communication of the data using the antenna; and the data source is arranged to provide a data signal for controlling the backscattering properties of the antenna to thereby transmit the data from the data source to the external communication system.

12. A combination of an implant device as claimed in claim 1 as a first implant device, along with a second implant device arranged to communicate with the first implant device.

13. A combination of an implant device as claimed in claim 1 and the external communication system that is arranged to transmit an electromagnetic wave from a transmitter toward the implant device and to receive a backscattered signal from the implant device at a receiver.

14. A combination as claimed in claim 13, wherein at least one of the electromagnetic wave is a radio wave at a frequency approved for use with medical implants.

15. A combination as claimed in claim 13, wherein the transmitter comprises an on-body antenna.

16. A combination as claimed in claim 15, comprising multiple transmitting antennas configured to be placed at multiple locations on the body so as to act together in order to transmit the electromagnetic wave toward the implant device.

17. A combination as claimed in claim 16, wherein the external communication system is configured to be arranged to reduce an amount of coupled power at a receiver antenna due to the antenna by using the multiple transmitting antennas to make a null coupled signal at the receiver and increase a signal to interference ratio.

18. Use of an implant device as claimed in claim 1, comprising:

implanting or inserting the implant device into a patient; transmitting the electromagnetic wave toward the device from the external communication system that is outside of the body; controlling the backscattering properties of the antenna in order to thereby transmit the data from the data source using the backscattered signal from the antenna; and receiving the backscattered signal at the external communication system.

19. Use as claimed in claim 18, comprising:

using the implant device to gather medical information at one or more locations within the patient's body, and then transmitting the information out of the body via the backscatter communications with the external communication system.

20. The implant device as claimed in claim 1, wherein the implant device is configured for data communication rates of at least 12 Mbps and within a frequency range of 350 Mhz to 600 Mhz.

* * * * *